United States Patent [19]

Shutske

[11] Patent Number: 5,330,986
[45] Date of Patent: Jul. 19, 1994

[54] INDOLE-7-CARBOXAMIDE DERIVATIVES

[75] Inventor: Gregory M. Shutske, Flemington, N.J.

[73] Assignee: Hoechst-Roussel Pharmaceuticals Inc., Somerville, N.J.

[21] Appl. No.: 980,869

[22] Filed: Nov. 24, 1992

[51] Int. Cl.$^5$ .................. A61K 31/495; A61K 31/40; C07D 403/00; C07D 209/04
[52] U.S. Cl. ..................... 514/253; 514/414; 514/415; 514/419; 544/373; 544/295; 548/467; 548/490; 548/491; 548/492; 548/510
[58] Field of Search ............... 544/373, 295; 548/490, 548/491, 492, 467, 490, 491, 492, 510; 514/253, 419, 414, 415

[56] References Cited

U.S. PATENT DOCUMENTS

| 4,737,501 | 4/1988 | Tominago et al. | 544/373 |
|---|---|---|---|
| 5,084,455 | 1/1992 | Clemence et al. | 544/373 |
| 5,124,332 | 6/1992 | Wise et al. | 544/373 |

FOREIGN PATENT DOCUMENTS 2193633  2/1988  United Kingdom .

OTHER PUBLICATIONS

Romero et al, CA 116-21074f (1991).
Azria et al, CA 110-8041z (1988).
Palmer et al. CA 108-142835y (1988).
Asselin et al., J. Med. Chem., 29, 1009-1015 (1986).
Arzneim-Forsch/Drug Res., 39(I), No. 2, 187 (1989).

Primary Examiner—Cecilia Tsang
Attorney, Agent, or Firm—Jerome Rosenstock

[57]  ABSTRACT

This invention relates to indole-7-carboxamide derivatives of the formula

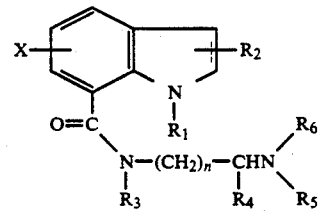

where $R_1$ through $R_6$ are independently H, loweralkyl, aryl, and aralkyl; and in addition $R_3$ and $R_5$ can be joined together to form a piperazine ring of the formula

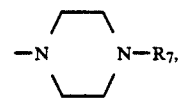

where $R_7$ is H, loweralkyl, aryl, arylloweralkyl, pyrimidyl; and $R_4$ and $R_5$ can be joined together to form a pyrrolidine ring of the formula

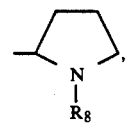

where $R_8$ is H, loweralkyl, aryl, arylloweralkyl; X is H, loweralkyl, halogen, $NO_2$, $CF_3$, $NH_2$, and $OR_9$; where $R_9$ is loweralkyl, arylloweralkyl and n is an integer of 1 to 3; and the pharmaceutically acceptable acid addition salts thereof and the optical isomers thereof where such isomers exist.

45 Claims, No Drawings

INDOLE-7-CARBOXAMIDE DERIVATIVES

To the best of our knowledge, the compounds of the present invention have not heretofore been described or suggested. UK Patent Application GB 2193 633 describes compounds useful for the treatment of stress-related psychiatric disorders, for increasing vigilance, for the treatment of rhinitis or serotonin-induced disorders. These compounds have the general formula A-B-C-D where the "A" group is selected from among nine substituents, including the substituent

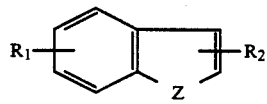

where $R_1$ and $R_2$ are selected from a group of at least ten further substituents, Z is selected from a group of four substituents including $NR_3$ where $R_3$ is selected from a further group of at least six substituents; the "B" group is selected from two substituents, including

the "C" group is selected from two substituents, including —NH—; and the "D" group is selected from at least fourteen substituents, including the group

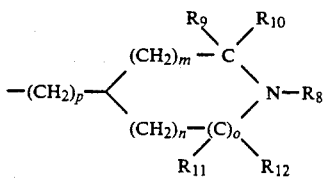

where $R_9$ to $R_{12}$ are independently selected from at least two substituents, m is 0, 1 or 2, and n, o, p are independently 0 or 1; and group

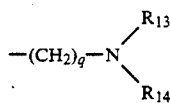

where q is 2 or 3 and $R_{13}$ and $R_{14}$ are independently ($C_{1-4}$) alkyl. In addition, the compounds

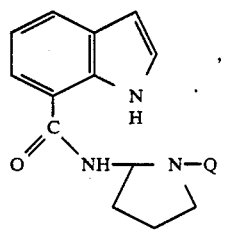

where Q is H or $CH_3$ are revealed.

The compounds of the present invention have the general formula

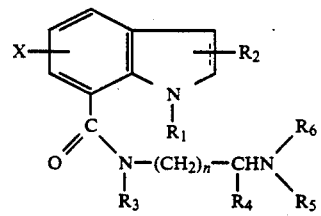

$R_1$ through $R_6$ are independently H, loweralkyl, aryl, and arylloweralkyl; and in addition $R_3$ and $R_5$ can be joined together to form a piperazine ring of the formula

where $R_7$ is H, loweralkyl, aryl, arylloweralkyl, pyrimidyl; and $R_4$ and $R_5$ can be joined together to form a pyrrolidine ring of the formula

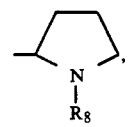

where $R_8$ is H, loweralkyl, aryl, arylloweralkyl; X is H, loweralkyl, halogen, $NO_2$, $NH_2$, $CF_3$ and $OR_9$; where $R_9$ is loweralkyl, arylloweralkyl; and n is an integer of 1 to 3; and the pharmaceutically acceptable acid addition salts thereof.

Throughout the specification and appended claims, a given chemical formula or name shall encompass all stereoisomers thereof where such isomers exist.

In the above definitions the term "lower" means the group it is describing contains from 1 to 6 carbon atoms. The term "alkyl" refers to a straight or branched chain hydrocarbon containing no unsaturation, e.g. methyl, ethyl, isopropyl, 2-butyl, neopentyl, n-hexyl, etc; the term "aryl" refers to a phenyl group of the formula

where Z and p are as defined below; the term "arylloweralkyl" refers to a monovalent substituent which consists of an aryl group, e.g., phenyl, o-toluene, m-methoxyphenyl, etc. linked through a lower alkylene group having its free valence bond from a carbon of the lower alkylene group, and having a formula of

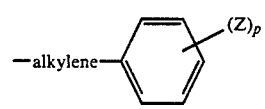

where Z is hydrogen, halogen, nitro, loweralkyl, loweralkoxy, loweracyl, $CF_3$, $NH_2$ and p is an integer of 1 to 3; the term "alkylene" refers to a bivalent radical of the lower branched or unbranched alkyl group it is derived from having valence bonds from two terminal carbons thereof, e.g. ethylene (—$CH_2CH_2$—), propylene (—$CH_2CH_2CH_2$—), isopropylene

etc.; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc.; and the term "halogen" refers to a member of the family consisting of fluorine, chlorine, bromine and iodine; the term pyrimidyl refers to a monovalent substituent which consists of a pyrimidyl group of the formula

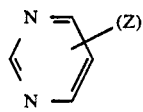

where Z is as defined above; the term loweracyl refers to a substituent having the formula, loweralkyl

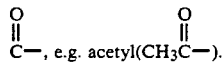

The compounds of the present invention are prepared in the following manner. The substituents $R_1$ through $R_6$ and the integer n are as defined earlier.

An indole-7-carboxylic acid of the formula

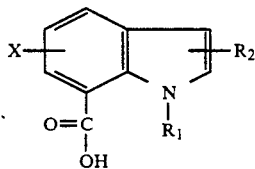

is selected. Such an indole (II), where $R_1$ is H, is well known and can be prepared generally in the manner described in Clark, R. D., Repke, D. B., Heterocycles, 22, 195 (1984), incorporated hereinto by reference, to form an ester of Compound II followed by hydrolysis of the resulting ester. Compounds II, where $R_1$ is not H, are prepared by reacting the aforementioned resultant ester with an alkyl halide of the formula $R_1$-halogen, where $R_1$ is not H. Typically, such a reaction is carried out in a polar aprotic solvent, e,g, tetrahydrofuran, dimethyl sulfoxide, N,N-dimethylfonnamide, at a temperature of 0° to 50° C. for 1 to 5 hours in the presence of a base, e.g. sodium hydride, potassium t-butoxide, lithium hexamethyldisilazide. The resulting ester is then hydrolyzed to the acid (II), where $R_1$ is not H.

The indole carboxylic acid II is then reacted directly under conventional amide formation procedures and conditions with an amine containing compound of the formula

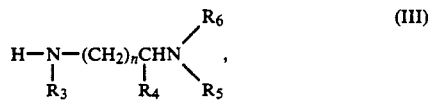

which are well known and can be prepared in a manner as described in Voigtlaender, W., Chemtech 11, 324 (1959); Hromataka, O., Kraupp, O., Skopalik, C., Monatsh. Chem., 84, 349 (1953); Baltzly, R., Buck, J. S., Ide, W. S., J. Am. Chem. Soc. 64, 2232 (1942); Hromatka, O., Skopalik, C., Monatsh. Chem. 83, 38 (1952); and Damiens, R., Ann. Chim. (Paris) 6, 835 (1951), to form Compound I of the invention.

Preferably, Compound II is first reacted with N,N-carbonyldiimidazole of the

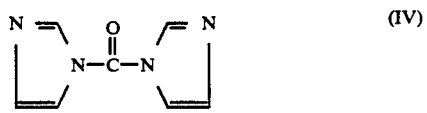

to form an acyl imidizole of the formula

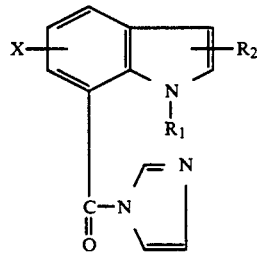

which, typically is then reacted, in situ, with Compound III to form Compound I of the invention. Typically, the reaction is carried out in a suitable polar, aprotic solvent, e.g. N,N-dimethylloweramide, N-methylpyrrolidinone, at a temperature of 0° to 50° C. for 1 to 5 hours to form Compound V and thereafter at a temperature of 0° to 50° C. for 1 to 5 hours to form Compound I of the invention. Compound I, where $R_3$ is not H, and $R_1$ is not H is prepared by reacting the compound I, where $R_3$ is not H and $R_1$ is H with an alkyl halide of the formula $R_1$-halogen, where R1 is not H. Typically, such a a reaction is carried out in a polar aprotic solvent, e.g. tetrahydrofuran, dimethyl sulfoxide, N,N-dimethylformamide at a temperature to 0° to 50° C. for 1 to 5 hours in the presence of a base, e.g. sodium hydride, potassium t-butoxide, lithium hexamethyldisilazide.

Compound I where the 2,3-bond is a single bond is prepared by reacting the compound I, where the 2,3-bond is a double bond, with a reducing agent such as sodium cyanoborohydride. Typically, such a reaction is carried out in an acidic solvent, e.g. acetic acid, propionic acid, methanolic hydrochloride acid at a temperature of 0° to 50° C. for 1 to 5 hours.

Compounds of the present invention are useful as analgesic agents due to their ability to alleviate pain in mammals. The activity of the compounds is demonstrated in the 1-phenyl-1,4-benzoquinone-induced writhing test in mice, a standard assay for analgesia [Proc. Soc. Exptl. Biol. Med., 95,729 (1957)]. The analgesic acitivity of some of the compounds expressed in terms of percent inhibition of writhing are given in Table I.

TABLE I

| | Dose mg/kg of body weight | inhibition of W writhing (%) |
|---|---|---|
| N-[2-(dimethylamino)ethyl]-1H-indole-7-carboxamide | (subcutaneous dose) 20 | 49 |
| N-[2-(dimethylamino)ethyl]-N-methyl-1H-indole-7-carboxamide(E)-2-butenedioate | 20 | 35 |
| N-[3-(dimethylamino)propyl]-1H-indole-7-carboxamide (E)-2-butenedioate (2:1) | 20 | 41 |
| 1-[(1-methyl-1H-indol-7-yl)carbonyl]-4-(2-pyrimidinyl)piperazine | 20 | 35 |
| 1-[2,3-dihydro(1H)-indol-7-yl)carbonyl]-4-[3-(trifluoromethyl)phenyl]piperazine | 20 | 33 |
| aspirin | 33 | 50 |

The analgesic relief of pain is achieved when the compounds of the invention are administered to a subject requiting such treatment at an effective oral, parenteral or intravenous does of from 0.1 to 100 mg/kg of body weight per day. A preferred effective dose within this range is from about 1 to 50 mg/kg of body weight per day. A particularly preferred effective amount is about 30 mg/kg of body weight per day. It is to be understood, however, that for any particular subject, specific dosage regimens should be adjusted according to the individual need. It is further to be understood that the dosages set forth herein are examples only and that they do not, to any extent, limit the scope of practice of the invention.

Examples of some of the compounds of the invention are:

N-(2-dimethylaminobutyl)-1H-indole-7-carboxamide;
N-(2-dimethylaminopropyl)-N-ethyl-1H-indole-7-carboxamide;
N-(2-dimethylaminoethyl)-N-ethyl-1-propyl-1H-indole-7-carboxamide;
1-[(1H-indol-7-yl)carbonyl]-4-(phenylmethyl)piperazine;
1-[(1H-indol-7-yl)carbonyl]-4-(5-methyl-2-pyrimidyl)piperazine;
1-[(5-methyl-1H-indol-7-yl )carbonyl]-4-ethylpiperazine;
1-[(5-chloro-1H-indol-7-yl)carbonyl]-4-propylpiperazine;
1-[(5-methoxy-1H-indol-7-yl)carbonyl]-4-(2-phenylethyl)piperazine;
1-[(1H-indol-7-yl)carbonyl]-4-(2,4-dichlorophenyl)piperazine; and
1-[(1H-indol-7-yl)carbonyl]-4-(2-methoxyphenyl)piperazine.

Effective amounts of the compounds of the present invention may be administered to a subject by one of various methods, for example, orally as in capsules or tablets, parenterally in the form of sterile solutions or suspensions, and in some cases intravenously in the form of sterile solutions. The compounds of the invention, while effective themselves, may be formulated and administered in the form of their pharmaceutically acceptable acid addition salts for purposes of stability, convenience of crystallization, increased solubility and the like.

Preferred pharmaceutically acceptable acid addition salts include those derived from inorganic acids such as hydrochloric, hydrobromic, sulfuric, nitric, phosphoric, perchloric acids and the like as well as organic acids such as tartaric, citric, succinic, maleic, fumaric acids and the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the indole-7-carboximide derivatives of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0–300 milligrams of the indole-7-carboxamide derivatives of the invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes, and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the indole-7-carboxamide derivative of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the indole-7-carboxamide derivative of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes and are not to be construed as limiting the invention disclosed herein. All temperatures are given in degrees centigrade.

EXAMPLES

I.
N-[2-(Dimethylamino)ethyl]-1H-indole-7-carboxamide

Indole-7-carboxylic acid (3.20 g, 0.020 mole) was dissolved in 50 ml of dimethylformamide (DMF) and 3.3 g (0.020 mole) of N,N'-carbonyldiimidazole was added. After stirring for 2 hours at room temperature, 2.0 g (0.023 mole) of N,N-dimethylethylenediamine was added, and stirring was continued for an additional 1 hour. At the end of this time the solvent was removed at a pressure of 0.1 mm Hg (50° C.) and the remaining residue was triturated with a minimum of H$_2$O and the crude product was filtered off and dried and concentrated to give a solid. Recrystallization from ether-pentane gave 2.20 g of N-[2-(dimethylamino)ethyl]-1H-indole-7-carboxamide (48%), m.p. 100°–102° C.

ANALYSIS: Calculated for C$_{13}$H$_{17}$N$_3$O: 67.50% C 7.41% H 18.17% N Found: 67.17% C 7.35% H 18.30% N

II.
N-[2-(Dimethylamino)ethyl]-N-methyl-1H-indole-7-carboxamide (E)-2-butenedioate Indole-7-carboxylic acid (3.20 g, 0.020 mole) was dissolved in 50 ml of dimethylformamide (DMF) and 3.3 g (0.020 mole) of N,N'-carbonyldiimidazole was added. After stirring for 2 hours at room temperature, 2.30 g (0.0225 mole) of N,N,N'-trimethylethylenediamine was added, and stirring was continued for an additional 1 hour. At the end of this time the solvent was removed at a pressure of 0.1 mm Hg (50° C.) and the remaining residue was triturated with a minimum of H$_2$O and the crude product filtered off and treated with an ethereal solution of fumaric acid to give N-[2-(dimethylamino)ethyl]-N-methyl-1H-indole-7-carboxamide (E)-2-butenedioate. Recrystallization from i-propanol gave 2.31 g (32%) of product, m.p. 154°–156° C.

ANALYSIS: Calculated for C$_{14}$H$_{19}$N$_3$O•C$_4$H$_4$O$_4$: 59.82% C 6.41% H 11.63% N Found: 59.70% C 6.45% H 11.82% N

III.
N-[3-(Dimethylamino)propyl]-1H-indole-7-carboxamide (E)-2-butenedioate (2:1)

Indole-7-carboxylic acid (3.20 g, 0.020 mole) was dissolved in 50 ml of dimethylformamide (DMF) and chilled with an ice-H$_2$O bath. N,N'-Carbonyldiimidazle (3.3 g, 0.020 mole) was then added and the reaction mixture was allowed to stir for 1 hour in the cold. At the end of this time, 3-dimethylaminopropylamine (2.5 g, 0.024 mole) was added and the cold bath was removed. After an additional 1 hour the DMF was removed from the reaction mixture under reduced pressure. The residue was triturated with a minimum of water and the crude product filtered off, dried, and treated with fumaric acid in ether. Recrystallization from isopropanol gave N-[3-(Dimethylamino)propyl]-1H-indole-7-carboxamide (E)-2-butenedioate (2.13 g, 35%), m.p. 160°–162° C.

ANALYSIS: Calculated for C$_{14}$H$_{19}$N$_3$O•0.5C$_4$H$_4$O$_4$: 63.35% C 6.98% H 13.85% N Found: 63.35% C 6.98% H 13.83% N

IV. 1-(1H-Indol-7-ylcarbonyl)-4-methylpiperazine

Indole-7-carboxylic acid (3.20 g, 0.020 mole) was dissolved in 30 ml of dimethylformamide (DMF) and chilled with an ice-water bath. N,N'-Carbonyldiimidazole was added (3.3 g, 0.020 mole) and the reaction mixture was stirred for 1 hour in the cold. At the end of this time N-methylpiperazine was added (2.5 g, 0.025 mole) and the reaction was allowed to come to room temperature overnight (about 16 hours). The DMF was removed under reduced pressure and the residue was passed over a column of basic alumina (50% methanol-ether) to remove residual imidazole. Recrystallization of the product from CH$_2$Cl$_2$-pentane gave 2.35 g (48%) of 1-(1H-indole-7-ylcarbonyl)-4-methylpiperazine, m.p. 176°–178° C.

ANALYSIS: Calculated for C$_{14}$H$_{17}$N$_3$O: 69.11% C 7.04% H 17.27% H Found.: 69.04% C 7.17% H 17.31% N

V.
N-[1-ethyl-2-pyrrolidinyl)methyl]-1H-indol-7-carboxamide (E)-2-butenedioate (2:1)

Indole-7-carboxylic acid (3.20 g, 0.020 mole) was dissolved in dimethylformamide (DMF) and chilled in an ice-water bath. N,N'-Carbonyldiimidazole was then added (3.3 g, 0.02 mole) and the reaction mixture was stirred for 1 hour in the cold. 2-(Aminomethyl)-1-ethylpyrrolidine was then added (3.2 g, 0.025 mole) and the reaction mixture was allowed to come to room temperature overnight. At the end of this time the volatiles were evaporated under reduced pressure and the residue was passed over a column of basic alumina (20% methanol-ether). Concentration of the product-containing fractions gave the product as a solid, which was convened to the fumaric acid salt in ether in the same manner as in Example II. Two recrystallizations from methanol gave N-[1-ethyl-2-pyrrolidinyl)methyl]-1H-indol-7-carboxamide (E)-2-butenedioate (2:1), [2.62 g, 40%], m.p. 208°–210° C.

ANALYSIS: Calculated for C$_{16}$H$_{21}$N$_3$O•0.5C$_4$H$_4$O$_4$: 65.63% C 7.04% H 12.76% N Found: 65.57% C 7.09% H 12.86% N

VI. 1-(1H-Indole-7-ylcarbonyl)-4-phenylpiperazine

Indole-7-carboxylic acid (3.20 g, 0.02 mole) was dissolved in 30 ml of dimethylformamide (DMF) and chilled with ice-water. N,N'-Carbonyldiimidazole (3.30 g, 0.02 mole) was then added and the reaction mixture was allowed to stir for 1 hour. At the end of this time N-phenylpiperazine (4.0 g, 0.025 mole) was added, the cold bath was removed., and the reaction mixture was allowed to come to room temperature over 3 hours. The product was filtered off and recrystallized form toluene to give 3.30 g (54%) of 1-(1H-indol-7-ylcarbonyl)-4-phenylpiperazine, m.p. 217°–219° C.

ANALYSIS: Calculated for C$_{19}$H$_{19}$N$_3$O: 74.73% C 6.27% H 13.76% N Found: 74.93% C 6.28% H 13.59% N

VII.
4-(4-Fluorophenyl)-1-(1H-indol-7-ylcarbonyl)piperazine

Indole-7-carboxylic acid (3.20 g, 0.02 mole) was dissolved in 30 ml of DMF and chilled with ice-water as N,N'-carbonyldiimidazole (3.3 g, 0.02 mole) was added. After stirring 1 hour in the cold, 1-4(4-fluorophenyl)-piperazine (4.50 g. 0.025 mole) was added in one portion. A precipitate had formed which was filtered off and washed well with ether. Recrystallization from tolune gave 3.72 g (58%) of 4-(4-fluorophenyl)-1-(1H-indol-7-ylcarbonyl)piperazine, m.p. 222°-224° C.

ANALYSIS: Calculated for $C_{19}H_{18}FN_3O$: 70.57% C 5.61% H 13.00% N Found: 70.75% C 5.77% H 12.85% N

VIII.
4-(4-(Acetylphenyl)-1-(1H-indol-7-ylcarbonyl)piperazine

To a cooled solution of indole-7-carboxylic acid (3.22 g; 20 mmoles) in 30 ml dimethylformamide was added 1,1'-carbonyldiimidazole (3.24 g; 20 mmoles). This was stirred for 50 minutes at ice bath temperature at which time 4-(4-acetylphenyl)piperazine was added to the reaction. This was stirred for 2 hours at ambient temperature. The solvent was then concentrated off and the resulting oil was triturated with water and filtered to give a solid. The solid was recrystallized from methanol:water to give 5.31 g (76%) of 4-(4-(Acetylphenyl)-1-(1H-indol-7-ylcarbonyl)piperazine, m.p. 189°-191° C.

ANALYSIS: Calculated for $C_{21}H_{21}N_3O_2$: 72.60% C 6.09% H 12.01% N Found: 72.39% C 6.35% H 12.11% N

IX.
1-(1H-Indol-7-ylcarbonyl)-4-(2-pyrimidinyl)piperazine

To a chilled solution of indole-7-carboxylic acid (3.22 g; 0.02 mole) in 30 ml dimethylformamide was added 1,1'-carbonyldiimidazole (3.24 g; 0.02 mole). This was stirred at ice bath temperature for 40 minutes after which a solution of 1-(2-pyrimidyl)piperazine (4.1 g; 0.025 moles) was added. This was stirred at ambient temperature for 3 hours and the solvent was concentrated in vacuo. The resulting oil was triturated with water to give 5.7 g (93%) of a solid, m.p. 194°-197° C. The solid was recrystallized from methanol/water to give 4.7 g (76%) of 1-(1H-Indol-7-ylcarbonyl)-4-(2-pyrimidinyl)piperazine, m.p. 200°-202° C.

ANALYSIS: Calculated for $C_{17}H_{17}N_5O$: 66.43% C 5.58% H 22.79% N Found: 66.05% C 5.84% H 22.93% N

X.
1-[(1-Methyl-1H-indol-7-yl)carbonyl]-4-(2-pyrimidinyl)piperazine

A solution of 1-[(1H-indol-7-yl)carbonyl]-4-(2-pyrimidyl)piperazine of Example IX, (2.50 g; 8.13 mmoles) in 40 ml dimethylformamide was added to a suspension of sodium hydride (470 mg; 9.76 mmoles) in DMF. This was followed by the addition of methyl iodide (0.51 ml; 8.13 mmoles). The reaction was quenched into water and extracted thrice with ethyl acetate. The organics were washed with water and dried (MgSO4). The reaction mixture was concentrated to give 2.37 g (91%) of a solid, m.p. 157°-160° C. The resultant compounds was then recrystallized from methanol/water to give 2.15 g (81%) of 1-[(1-Methyl-1H-indol-7-yl)carbonyl]-4-(2-pyrimidinyl)piperazin m.p. 159°-160° C.

ANALYSIS: Calculated for $C_{18}H_{19}N_5O$: 67.27% C 5.96% H 21.79% N Found: 66.85% C 6.04% H 21.61% N

XI.
1-(1H-Indole-7-ylcarbonyl)-4-[3-(trifluoromethyl)-phenyl]piperazine

To a cooled solution of indole 7-carboxylic acid (3.22 g; 0.02 moles) in 30 ml dimethylformamide was added N,N'-carbonyldiimidazole (3.24 g; 0.02 moles). After 45 minutes, a solution of 4-(3-(trifluoromethyl)phenyl)piperazine (5.76 g; 0.025 moles) in 10 ml DMF was added. This was stirred for 18 hours at ambient temperature. The solvent was then concentrated off and the resulting oil was partitioned between ethyl acetate and water. The aqueous was extracted twice with ethyl acetate and the organics were washed with water and dried (saturated NaCl, MgSO4). The desired amine was purified via flash chromatography (10% ethyl acetate/dichloromethane), to give 5.6 g (77%) of a solid, m.p. 147°-151° C. The solid was recrystallized from methanol to give 3.14 g (43%) of 1-(1H-indol-7-ylcarbonyl)-4-[3(trifuoromethyl)phenyl]piperazine, m.p. 149°-151° C.

ANALYSIS: Calculated for $C_{20}H_{18}F_3N_3O$: 64.33% C 4.86% H 11.25% N Found: 64.21% C 4.78% H 11.05% N

XII.
1-[(2,3-Dihydro-1H-indol-7-yl)carbonyl]-4-[3(trifluoromethyl)phenyl]piperazine To a solution of 1-(1H-indol-7-ylcarbonyl]-4-[3(trifluoromethyl)phenyl]piperazine of Example XI, (8.75 g, 23.4 mmoles) in 60 ml glacial acetic acid was added sodium cyanoborohydride (4.7 g; 78.4 mmoles). This was stirred for 2 hours then added to iced water, extracted thrice with ethyl acetate and the combined organics were washed with water and dried (saturated NaCl, MgSO4 ). The desired compounds was purified via flash chromatography (ether/hexane, 3:1) to give 4.05 g (46%) of crystals, m.p. 113°-117° C. This was recrystallized from methanol/water to give 3.53 g (40%) of 1-[(2,3-dihydro-1H-indol-7-yl)carbonyl]-4-[3-(trifluoromethyl)phenyl]piperazine, m.p. 115°-118° C.

ANALYSIS: Calculated for $C_{20}H_{20}F_3N_3O$: 63.99% C 5.37% H 11.19% N Found: 63.98% C 5.42% H 11.29% N

I claim:

1. A compound of the formula

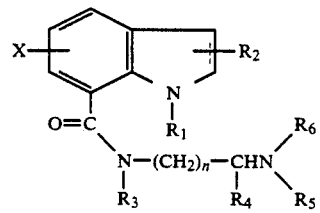

where $R_1$ and $R_2$ are independently H, loweralkyl and arylloweralkyl; wherein $R_3$ through $R_6$ are independently selected from aryl, arylloweralkyl, and in addition $R_3$ and $R_5$ can be joined together to form a piperazine ring of the formula

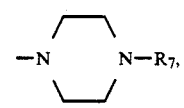

where $R_7$ is H, loweralkyl, aryl, arylloweralkyl, pyrimidyl; and $R_4$ and $R_5$ can be joined together to form a pyrrolidine ring of the formula

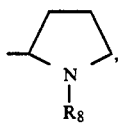

where $R_8$ is H, loweralkyl, aryl, arylloweralkyl; X is H, loweralkyl, halogen, $NO_2$, $NH_2$, $CF_3$ and $OR_9$ where $R_9$ is loweralkyl, arylloweralkyl and n is an integer of 1 to 3; and the pharmaceutically acceptable acid addition salts thereof and the optical isomers thereof where such isomers exist.

2. The compound of claim 1 wherein n is 1.

3. The compound as defined in claim 1 wherein $R_4$ and $R_5$ are joined to form said pyrrolidine ring.

4. The compound as defined in claim 3 wherein n is 2 or 3.

5. The compound as defined in claim 1 wherein $R_3$ and $R_5$ are joined to form said piperazine ring.

6. The compound as define in claim 1 which is 1-(1H-indol-7-ylcarbonyl)-4-phenylpiperazine and the acceptable acid addition salts thereof.

7. The compounds as defined in claim 1 which is 4-(4-fluorophenyl)-1-(1H-indol-7-ylcarbonyl)piperazine and the acceptable acid addition salts thereof.

8. The compound as defined in claim 1 which is 4-(4-acetylphenyl)-1-(1H-indol-7-ylcarbonyl)piperazine and the acceptable acid addition salts thereof.

9. The compound as defined in claim 1 which is 1-(1H-indol-7-ylcarbonyl)-4-(2-pyrimidinyl)piperazine and the acceptable acid addition salts thereof.

10. The compound as defined in claim 1 which is 1-[(1-methyl-1H-indol-7-yl)carbonyl]-4-(2-pyrimidinyl)piperazine and the acceptable acid addition salts thereof.

11. The compound as defined in claim 1 which is 1-(1H-indol-7-ylcarbonyl]-4-[3-(trifluoromethyl)-phenyl]piperazine and the acceptable acid addition salts thereof.

12. The compound as defined in claim 1 which is 1-[(2,3-dihydro-1H-indol-7-yl)carbonyl]-4-[3-(trifluoromethyl)piperazine and the acceptable acid addition salts thereof.

13. An analgesic composition which comprises an effective pain alleviating amount of a compound of the formula

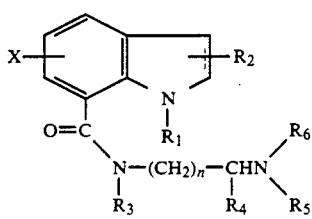

where $R_1$ and $R_2$ are independently H, loweralkyl and arylloweralkyl; wherein $R_3$ through $R_6$ are independently selected from aryl, arylloweralkyl, and in addition $R_3$ and $R_5$ can be joined together to form a piperazine ring of the formula

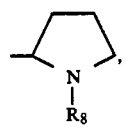

where $R_7$ is H, loweralkyl, aryl, arylloweralkyl, pyrimidyl; and $R_4$ and $R_5$ can be joined together to form a pyrrolidine ring of the formula where $R_8$ is H, loweralkyl, aryl, arylloweralkyl; X is H, loweralkyl, halogen, $NO_2$, $NH_2$, $CF_3$ and $OR_9$ where $R_9$ is loweralkyl, arylloweralkyl and n is an integer of 1 to 3: and the pharmaceutically acceptable acid addition salts thereof and the optical isomers there where such isomers exist; and a suitable carrier therefor.

14. The analgesic composition as defined in claim 13 wherein n is 1.

15. The analgesic composition as defined in claim 13 wherein $R_4$ and $R_5$ are joined to form said pyrrolidine ring.

16. The analgesic composition as defined in claim 13 wherein n is 2 or 3.

17. The analgesic composition as defined in claim 13 wherein $R_3$ and $R_5$ are joined to form said piperazine ring.

18. The analgesic composition as defined in claim 13 which comprises 1-(1H-indol-7-ylcarbonyl)-4-methylpiperazine and the acceptable acid addition salts thereof.

19. The analgesic composition as defined in claim 13 which comprises 1-(1H-indol-7-ylcarbonyl)-4-phenylpiperazine and the acceptable acid addition salts thereof.

20. The analgesic composition as defined in claim 13 which comprises 4-(4-fluorophenyl)-1-[(1H-indol-7-ylcarbonyl)piperazine and the acceptable acid addition salts thereof.

21. The analgesic composition as defined in claim 13 which comprises 4-(4-acetylphenyl)-1-(1H-indol-7-ylcarbonyl)piperazine and the acceptable acid addition salts thereof.

22. The analgesic composition as defined in claim 13 which comprises 1-(1H-indol-7-ylcarbonyl)-4-(2-pyrimidinyl)piperazine and the acceptable acid addition salts thereof.

23. The analgesic composition as defined in claim 13 comprises 1-[(1-methyl-1H-indol-7-yl)carbonyl]4-2-pyrimidinyl)piperazine and the acceptable acid addition salts thereof.

24. The analgesic composition as defined in claim 13 which comprises 1-(1H-indol-7-ylcarbonyl]-4-[3(trifluoromethyl)phenyl]piperazine and the acceptable acid addition salts thereof.

25. The analgesic composition as defined in claim 13 which comprises 1-[(2,3-dihydro-1H-indol-7-yl)carbonyl]-4-[3-(trifuoromethyl)phenyl]piperazine and the acceptable acid addition salts thereof.

26. A method of alleviating of pain in a mammal which comprises administering to a mammal a pain alleviating effective amount of a compound of the formula

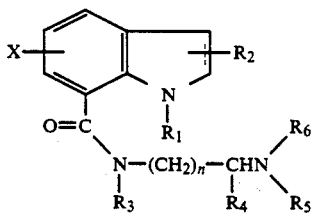

where $R_1$ and $R_2$ are independently H, loweralkyl, aryl, and arylloweralkyl; wherein $R_3$ through $R_6$ are independently selected from aryl, arylloweralkyl, and in addition $R_3$ and $R_5$ can be joined together to form a piperazine ring of the formula

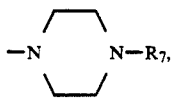

where $R_7$ is H, loweralkyl, aryl, arylloweralkyl, pyrimidyl; and $R_4$ and $R_5$ can be joined together to form a pyrrolidine ring of the formula

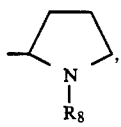

where $R_8$ is H, loweralkyl, arylloweralkyl; X is H, loweralkyl, halogen, $NO_2$, $CF_3$ and $OR_9$, where $R_9$ is loweralkyl, arylloweralkyl; and n is an integer of 1 to 3; and the pharmaceutically acceptable salts thereof and the optical isomers thereof where such isomers exist.

27. The method of claim 26 wherein n is 1.
28. The method of claim 26 wherein $R_4$ and $R_5$ are joined to form said pyrrolidine ring.
29. The method of claim 28 wherein n is 2 or 3.
30. The method of claim 26 wherein $R_3$ and $R_5$ are joined to form said piperazine ring.
31. The method of claim 26 wherein said compound is N-[2(dimethylamino)ethyl]-1H-indole-7-carboxamide and the acceptable acid addition salts thereof.
32. The method of claim 26 wherein said compounds is N-[2(dimethylamino)ethyl]-N-methyl-1H-indole-7-carboxamide and the acceptable acid addition salts thereof.
33. The method of claim 32 wherein said salt is the (E)-2-butenedioate.
34. The method of claim 26 wherein said compound is N-[3-(dimethylamino)propyl]-1H-indole-7-carboxamide and the acceptable acid addition salts thereof.
35. The method of claim 34 wherein said salt is the 2:1 (E)-2-butenedioate.
36. The method of claim 26 wherein said compound is 1-(1H-indol7-ylcarbonyl)-4-methylpiperazine and the acceptable acid addition salts thereof.
37. The method of claim 26 wherein said compound is N-[(1(ethylpyrrolidinyl)methyl]-1H-indole-7-carboxamide and the acceptable acid addition salts thereof.
38. The method of claim 37 wherein said salt is the 2:1 (E)-2-butenedioate.
39. The method of claim 26 wherein said compound is 1-(1H-indol-7-ylcarbonyl)-4-phenylpiperazine and the acceptable acid addition salts thereof.
40. The method of claim 26 wherein said compound is 4-(4-fluorophenyl)-1-(1H-indol-7-ylcarbonyl)piperazine and the acceptable acid addition salts thereof.
41. The method of claim 26 wherein said compound is 4-(4-acetylphenyl)-1-(1H-indol-7-ylcarbonyl)piperazine and the acceptable acid addition salts thereof.
42. The method of claim 26 wherein said compound is 1-(1H-indol-7-ylcarbonyl)-4-(2-pyrimidinyl)piperazine and the acceptable acid addition salts thereof.
43. The method of claim 26 wherein said compound is 1-[(1-methyl-1H-indol-7-yl)carbonyl]-4-(2-pyrimidinyl)piperazine and the acceptable acid addition salts thereof.
44. The method of claim 26 wherein said compound is 1-(1H-indol-7-ylcarbonyl)-4-[3-(trifluoromethyl)-phenyl]piperazine and the acceptable acid addition salts thereof.
45. The method of claim 26 wherein said compound is 1-[(2,3-dihydro-1H-indol-7-yl )carbonyl]-4-[3-(trifluoromethyl)phenyl]piperazine and the acceptable acid addition salts thereof.

* * * * *